US010245817B2

(12) United States Patent
Andjelic et al.

(10) Patent No.: US 10,245,817 B2
(45) Date of Patent: Apr. 2, 2019

(54) METHOD OF LAMINATING ABSORBABLE SEMI-CRYSTALLINE POLYMERIC FILMS

(71) Applicant: Ethicon, Inc., Somerville, NJ (US)

(72) Inventors: Sasa Andjelic, Nanuet, NY (US); Dominick Egidio, Flanders, NJ (US)

(73) Assignee: Ethicon, Inc., Somerville, NJ (US)

( * ) Notice: Subject to any disclaimer, the term of this patent is extended or adjusted under 35 U.S.C. 154(b) by 221 days.

(21) Appl. No.: 15/267,700

(22) Filed: Sep. 16, 2016

(65) Prior Publication Data

US 2018/0079192 A1 Mar. 22, 2018

(51) Int. Cl.

| | |
|---|---|
| *B32B 37/10* | (2006.01) |
| *A61L 31/04* | (2006.01) |
| *A61L 31/10* | (2006.01) |
| *A61L 31/14* | (2006.01) |
| *B29C 47/00* | (2006.01) |
| *B29C 55/30* | (2006.01) |
| *B32B 5/02* | (2006.01) |
| *B32B 27/12* | (2006.01) |
| *B32B 37/06* | (2006.01) |
| *B32B 27/00* | (2006.01) |
| *B32B 37/15* | (2006.01) |
| *A61K 9/70* | (2006.01) |
| *B29C 47/92* | (2006.01) |
| *A61F 2/00* | (2006.01) |
| *B29L 31/00* | (2006.01) |
| *B32B 37/00* | (2006.01) |

(52) U.S. Cl.
CPC ............ *B32B 37/10* (2013.01); *A61K 9/7007* (2013.01); *A61L 31/042* (2013.01); *A61L 31/048* (2013.01); *A61L 31/10* (2013.01); *A61L 31/14* (2013.01); *A61L 31/148* (2013.01); *B29C 47/0004* (2013.01); *B29C 47/0021* (2013.01); *B29C 47/0057* (2013.01); *B29C 47/0064* (2013.01); *B29C 47/92* (2013.01); *B29C 55/30* (2013.01); *B32B 5/022* (2013.01); *B32B 5/024* (2013.01); *B32B 5/028* (2013.01); *B32B 27/00* (2013.01); *B32B 27/12* (2013.01); *B32B 37/06* (2013.01); *B32B 37/15* (2013.01); *A61F 2/0063* (2013.01); *A61L 2420/02* (2013.01); *B29C 47/0066* (2013.01); *B29C 2947/92704* (2013.01); *B29C 2947/92942* (2013.01); *B29C 2947/92961* (2013.01); *B29K 2995/004* (2013.01); *B29L 2031/753* (2013.01); *B32B 2037/0092* (2013.01); *B32B 2305/10* (2013.01); *B32B 2535/00* (2013.01)

(58) Field of Classification Search
CPC ....... A61F 2/0063; B29C 47/00; B29C 55/30; B29C 47/0066; B29C 47/0057; B29C 47/0021; B32B 37/10; B32B 37/06; B32B 27/12; B32B 5/028; B32B 5/024; B32B 5/022; B32B 2305/10; B32B 27/00; B32B 37/15; B32B 2037/0092; B32B 2535/00; B29L 2031/753; A61L 2420/02; A61L 31/14; A61L 31/10; A61L 31/048; A61L 31/042; A61K 9/7007
See application file for complete search history.

(56) References Cited

U.S. PATENT DOCUMENTS

| | | | |
|---|---|---|---|
| 2,269,125 | A | 1/1942 | Quenelle et al. |
| 3,364,200 | A | 1/1968 | Ashton et al. |
| 3,467,565 | A | 9/1969 | Utz et al. |
| 3,932,693 | A | 1/1976 | Shaw et al. |
| 4,119,481 | A | 10/1978 | Beckley |
| 4,475,971 | A | 10/1984 | Canterino |
| 4,664,859 | A | 5/1987 | Knoop |
| 4,942,087 | A | 7/1990 | Motooka et al. |
| 5,133,739 | A | 7/1992 | Bezwada et al. |
| 5,180,398 | A | 1/1993 | Boardman et al. |
| 5,510,176 | A | 4/1996 | Nakamura et al. |
| 5,629,077 | A | 5/1997 | Turnlund et al. |
| 6,911,244 | B2 | 6/2005 | Blemberg et al. |
| 7,615,065 | B2 | 11/2009 | Priewe et al. |
| 7,943,683 | B2 | 5/2011 | Rizk et al. |
| 8,030,434 | B2 | 10/2011 | Ikeda et al. |
| 8,278,409 | B2 | 10/2012 | Modesto et al. |
| 8,349,354 | B2 | 1/2013 | Andjelic |
| 8,821,585 | B2 | 9/2014 | Pfeiffer et al. |
| 2002/0034610 | A1* | 3/2002 | Perez ..................... B32B 27/12 428/141 |
| 2008/0095978 | A1* | 4/2008 | Siqueira ............. A61F 13/4902 428/137 |
| 2013/0001782 | A1 | 1/2013 | Otsuka et al. |

OTHER PUBLICATIONS

Bezwada, R.S. et al. "Monocryl® suture, a new ultra-pliable absorbable monofilament suture". *Biomaterials*, vol. 16, (1995) pp. 1141-1148, Elsevier Science Limited.

* cited by examiner

*Primary Examiner* — Vishal I Patel

(74) *Attorney, Agent, or Firm* — David E. Crichton; Leo B. Kriksunov

(57) ABSTRACT

The invention relates to novel processes for the lamination of semi-crystalline, high-melting point, low glass transition polymeric films, which are extruded and subsequently laminated on various thermally sensitive substrates to form laminated medical device constructs in a specific time interval to allow low processing temperatures to avoid polymer film and/or substrate degradation or heat-related distortions. Also disclosed are laminated medical device constructs made from such processes.

10 Claims, No Drawings

METHOD OF LAMINATING ABSORBABLE SEMI-CRYSTALLINE POLYMERIC FILMS

FIELD OF THE INVENTION

The field of art to which this invention relates is novel methods for the lamination of absorbable, semi-crystalline, high melting polymeric films on various thermally sensitive substrates for absorbable and partially absorbable medical applications.

BACKGROUND OF THE INVENTION

Synthetic absorbable polyesters are well known in the art. The terms absorbable, bioabsorbable, bioresorbable, resorbable, biodegradable are used herein interchangeably. The open and patent literature particularly describe polymers and copolymers made from glycolide, L(−)-lactide, D(+)-lactide, meso-lactide, epsilon-caprolactone, p-dioxanone, and trimethylene carbonate.

Medical devices in the form of polymeric films or a composite structure containing a substrate and a laminated film are known in the art and have utility in a variety of surgical applications including tissue repair, hernia repair, organ repair, etc.

Absorbable films and processes for forming such films from bioabsorbable polymeric materials have also been described by various researchers over the years, e.g., U.S. Pat. No. 7,943,683 B2, "Medical Devices Containing Oriented Films of Poly-4-hydroxybutyrate and Copolymers"; U.S. Pat. No. 8,030,434 B2, "Polyester Film, Process for Producing the Same and Use Thereof"; U.S. Pat. No. 4,942,087A, "Films of Wholly Aromatic Polyester and Processes for Preparation Thereof"; U.S. Pat. No. 4,664,859A, "Process for Solvent Casting a Film"; and, U.S. Pat. No. 5,510,176A, "Polytetrafluoroethylene Porous Film". Various conventional methodologies and processes are known and exist to produce polymeric films. They include, but are not limited to, melt extrusion, solvent casting, and compression molding. However, not all polymers can be easily converted to film products; additionally, different conversion techniques have different challenges. In the case of melt extrusion, the resin must be thermally stable, exhibiting an appropriate melt viscosity, i.e., not too low so as to cause "dripping" and not too high so as to develop excessively high pressures in the extruder, causing instability and non-uniform results. In the case of resins possessing low glass transition temperatures, the dimensional stability of the films made therefrom may be very low if the polymer morphology includes some chain orientation. This is a great driving force for shrinkage and distortion. To circumvent dimensional instability difficulties, the development of a certain amount of crystallinity in the film is advantageous. The rate of crystallization is important in establishing a robust film extrusion process, while the overall level of crystallinity is important in achieving dimensional stability and good mechanical properties. It is known that a crystallinity level that is too low will result in films which may distort upon ethylene oxide sterilization or upon exposure to even mildly elevated temperatures during processing, transportation, or storage. In certain surgical applications, it is desirable for the final films to be strong with appropriate tear resistance, yet pliable enough to possess good handling characteristics. Examples of such surgical applications include hernia film-containing repair patches requiring suturing and/or tacking as a means of fixation to the surrounding tissues, various film-based medical devices that undergo extensive handling and manipulation prior to implantation, in cases where the film is a load-bearing component, etc.

An absorbable polymer used to manufacture films must possess certain melt and thermal properties, certain crystallization characteristics, as well as certain mechanical and hydrolysis properties, if it is to be suitable for fabricating surgical film products by a melt extrusion process. In the case of films made by solution casting, the polymer resin needs to possess appropriate solubility in a suitable solvent. Suitable solvents advantageously have an appropriate vapor pressure curve leading to suitable evaporation rates, and are generally non-toxic. The polymer must then possess certain solubility and crystallization characteristics, as well as certain mechanical and hydrolysis properties, if it is to be suitable for fabricating surgical film products by a solvent casting process.

Methods of laminating a polymeric film on different substrates have been described in the patent literature. For instance, U.S. Pat. No. 8,349,354B2 (Andjelic) describes a hemostatic composite structure having an absorbable fabric or non-woven substrate and continuous non-porous polymeric film that is laminated on one major surface of the substrate. However, the film layer is limited to an amorphous polymeric material, or semi-crystalline polymeric material having a melting point temperature below 120° C.

For the lamination of polymeric films having a melting point temperature significantly higher than 120° C. (e.g., around 200° C.), different approaches have been used and disclosed in the prior art, including the addition of an adhesive layer between the high melting point polymeric film and a substrate as described in U.S. Pat. No. 7,615,065 and U.S. Pat. No. 8,821,585 B2. In the market place, the ETHICON PHYSIOMESH™ mesh device is a commercially available hernia mesh product that is made from an absorbable polymer film (based on 75/25 Gly/Cap resin) coupled with a non-absorbable polypropylene mesh. To join the high melting point polymeric film onto the mesh, an interlayer of lower melting point poly (p-dioxanone)-based film (melting point of 110° C.) is used on both sides of the mesh to glue these three structures together to form the composite structure. If no adhesive layer/film were used for bonding, a high temperature above 150° C. would be needed to bond the absorbable polymer film to the mesh, resulting in distortion and shrinkage of the mesh. On the other hand, the presence of an additional layer for bonding purposes increases the risk of adverse tissue reactions (more degradation products released such as free acids), biocompatibility, and increases device stiffness; it also significantly increases production cost and complicates the manufacture of such a medical device.

Similar to the technology mentioned above, U.S. Pat. No. 3,467,565A describes the lamination of a high melting plastic film, such as Nylon, onto a carrier web using a low melting plastic film, such as polyethylene. The disclosure is silent with respect to using this technology on absorbable polymer systems.

A method for forming strong cross-laminated flat films described in U.S. Pat. No. 4,475,971A comprises composite, coextruded film structures having a higher melting point layer and a lower melting point layer. The higher melting point layer may be polyethylene, nylon, polyester or polypropylene, while the lower melting point component is selected from the group consisting of an ethylene/vinyl acetate copolymer, a low density polyethylene polymer and an ethylene/propylene copolymer. Again, the low melting point component as a glue is used on all non-absorbable components.

U.S. Pat. No. 6,911,244B2 describes the encapsulated barrier for flexible films comprising a barrier layer made from a thermally sensitive material, preferably ethylene vinyl alcohol, and at least one substrate, preferably oriented polypropylene encapsulated by two or more adhesive layers. The adhesive layers, in addition to having a bonding function may also protect the barrier material from high temperatures of the hardware and long residence times within the hardware.

US 20130001782A1 teaches a method utilizing a low melting thin metallic film for lamination of a high melting point soldering layer on a three-layered structure for fabrication of a semiconductor device.

A biodegradable mesh and film stent for use in blood vessels is described in U.S. Pat. No. 5,629,077 comprising a sheet of a composite mesh material made from biodegradable high strength polymer fibers bonded together with a second biodegradable adhesive polymer, and laminated on at least one side with a thin film of a third biodegradable polymer. The lamination is achieved by heat bonding via a lower temperature adhesive biodegradable layer, such as epsilon-caprolactone or a low melting point temperature plurality of fibers in a mesh structure.

Laminated food packaging having a multilayered film structure and having low vapor and gas permeability is described in U.S. Pat. No. 3,932,693A. The structure comprises a base layer of an oriented polypropylene film laminated onto a layer of a vinylidene chloride polymer using a layer of ethylene/vinyl acetate copolymer film having vinyl acetate content greater than 10 percent by weight.

U.S. Pat. No. 4,119,481A describes a fusion laminated high-temperature fabric made of amorphous silica fibers with a thermoplastic film made from vinyl, polyester or urethane polymers using high energy infra-red radiation. The high energy is preferentially absorbed in a short time and space resulting in an increase in temperature sufficient to produce the desired degree of adhesion with the thermoplastic film. Although this method of lamination does not require an additional adhesive element, the use of high energy radiation can cause degradation in cases where fabric and/or film are made from absorbable polymers.

A method of making laminated Nylon-based fabrics is described in U.S. Pat. No. 2,269,125A. The method provides for treating the fabric with water for easier heat pressure bonding. The absorbed moisture lowers significantly the glass transition temperature and increases thermal conductivity of Nylon-based fibers allowing for the lower lamination temperatures. However, the use of moisture with heat on absorbable polymer structures would cause significant polymer degradation.

In summary, there is a strong, continuing need in this art for novel methods that will effectively laminate high melting temperature, semi-crystalline absorbable films on various thermally sensitive absorbable or non-absorbable substrates without the need for any additional adhesive layer or any type of glue substance, including moisture. The lamination of thermally sensitive substrates needs to be conducted using low lamination temperatures, such as 120° C. or lower, to avoid chemical degradation and physical distortions and novel methods are needed to provide for the lamination of such substrates.

SUMMARY OF THE INVENTION

Accordingly, novel lamination methods and laminated medical device constructs are disclosed.

One aspect of the present invention is a method of manufacturing a laminated medical device construct. A semicrystalline polymer film is extruded, the polymer film having a melting point temperature of 140° or higher, a glass transition temperature below 25° C., and a crystallinity, wherein said polymer film is crystallizable at room/ambient conditions.

The polymer film is laminated to a thermally sensitive polymeric substrate to form a laminated medical device construct by conducting a thermal/pressure laminating step within about 10 minutes after the extrusion of the polymer film wherein said film has a crystallinity of about 10% or less and is laminated onto the substrate at a temperature of about 120° C. or lower, such that the substrate is not damaged or degraded and the film is effectively laminated to the substrate.

Another aspect of the present invention is a method of manufacturing a laminated medical device construct. A semicrystalline polymer film is extruded, the polymer film having a melting point temperature of 140° or higher, a glass transition temperature above 25° C., and a crystallinity.

The polymer film is laminated to a thermally sensitive polymeric substrate to form a laminated medical device construct by conducting a thermal/pressure laminating step within about 10 minutes after the extrusion of the polymer film wherein said film has a crystallinity of about 10% or less and is laminated onto the substrate at a temperature of about 120° C. or lower, such that the substrate is not damaged or degraded and the film is effectively laminated to the substrate and wherein the laminated polymer film has an achievable crystallinity of at least about 10%.

Yet another aspect of the present invention is a method of laminating a polymer film to a thermally sensitive polymeric substrate. Initially, an absorbable polymer having a melt temperature is transferred to a hopper of a melt extruder outfitted with a slit die, with a barrel and die temperature within the range of about 10° C. above the melt temperature of the said absorbable polymer. The absorbable polymer is extruded through said slit die, thereby forming a film. The film is drawn between about 0.8× to about 10× such that the film has a thickness between 0.01 mil and 10 mil. In the time interval between 0 and 10 minutes following the film extrusion contact is provided between the freshly extruded polymeric film having crystallinity of about 10% or less, and the thermally sensitive polymeric substrate. Then, the film and substrate are heat pressed to form a laminated construct at temperatures of 120° C. or lower.

Still yet another aspect of the present invention is a laminated medical device construct made using any of the above-described methods.

DETAILED DESCRIPTION OF INVENTION

As used herein, the term "thermally sensitive polymeric substrate" is defined to mean a polymeric substrate in the form of mesh or non-woven or woven porous structure that undergoes chemical degradation or various physical distortions (e.g., shrinkage) upon being subjected to relatively high processing temperatures, such as temperatures of 140° C. or higher. Although it is preferred that the polymer films be made from absorbable polymers, in an alternate embodiment the polymer films may be made from non-absorbable polymers.

The term "achievable crystallinity of the laminated film" as used herein is defined to mean a maximum level of crystallinity that a polymeric film can achieve by applying various thermal and processing means, such as annealing.

The present invention is directed toward novel lamination methods suitable for a semicrystalline, polymeric film exhibiting a high melting point of 140° C. or higher, and having a glass transition temperature of 25° C. or lower. In a preferred embodiment, the polymeric film is absorbable. Such films may be laminated onto non-woven or woven, absorbable or non-absorbable polymer substrates, in particular thermally sensitive substrates, wherein the lamination is conducted at moderate processing temperature of 120° C. or lower. Another aspect of the present invention is a novel lamination method suitable for absorbable, semicrystalline, polymeric film exhibiting a melting point of 140° C. or higher, and a glass transition temperature higher than 25° C., with an achievable crystallinity level of 10% or higher in the laminated polymeric film. In a preferred embodiment, the polymeric film is absorbable. Such films may be laminated onto non-woven or woven, absorbable or non-absorbable polymer substrates, in particular thermally sensitive substrates, wherein the lamination is conducted at moderate processing temperature of 120° C. or lower.

The films made from the copolymers useful in the practice of the present invention may be used in a variety of medical applications including tissue separating barriers, reinforcing buttress materials, hemostasis, drug delivery and adhesion prevention. The films can be laminated with other devices (such as meshes and other textiles) to form multilayer structures.

In one embodiment, the film layer is made from a polymer material that is a semi-crystalline, absorbable polymer having the melting point above 140° C. In another embodiment, the film layer is made from a polymer material having a melting point temperature above 150° C., more preferably more than 180° C. In another embodiment, the film layer is made from a polymer material having a glass transition temperature of less than about 25° C. In another embodiment of the process of the present invention, the film layer is made from a polymer material that is a semi-crystalline, absorbable polymer having a melting point above 140° C. and having a glass transition temperature of greater than about 25° C., with an achievable crystallinity level in the laminated film of 10% or higher.

The present invention is also directed to a hemostatic composite structure having a bioabsorbable fabric or non-woven substrate having at least two major oppositely facing surface areas and a polymer-based film that is laminated on at least one major surface of said substrate. Hemostasis is achieved by applying a composite structure onto a wound site wherein a major surface of the substrate without the film layer is applied onto the wound site. The bioabsorbable fabric substrate can be an oxidized polysaccharide and/or the non-woven substrate can be made from bioabsorbable, non-cellulosic derived polymers. The polymer based film can be a conventional bioabsorbable polymer, such as a bioabsorbable polymer selected from the group consisting of poly(ethoxyethylene diglycolate-co-glycolide), poly(lactide), poly(glycolide), poly(amino acids) and copolymers and terpolymers thereof. This also includes homopolymers and copolymers of lactide and/or glycolide with lower melting components including caprolactone, p-dioxanone, trimethylene carbonate (TMC), polyethylene glycol, and various polyether ester formulations. In one embodiment, the substrate is made from oxidized regenerated cellulose and the top coat film is a copolymer, preferably 75/25 poly(glycolide-co-epsilon caprolactone). In a particularly preferred embodiment, the film has a thickness in the range of about 0.1 to 10 mils. In another embodiment, the polymer film made be made for a non-absorbable conventional polymer such as polypropylene, polyethylene, polyethylene terephthalate, Nylon, etc.

The laminated composite structures of the present invention can optionally further include a bioactive agent, such as a hemostatic agent, including hemostatic agents such as procoagulant enzymes, proteins and peptides, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. In one embodiment, the hemostatic agent is selected from the group consisting of thrombin, fibrinogen and fibrin.

The composite structure including a polymeric film and a substrate often exhibits better handling properties for surgical applications and settings. Many fabric or non-woven based hemostats do not have ideal handling characteristics as they wrinkle and fold during surgical procedures especially in the presence of blood or other fluids. The substrate/film composites of the present invention minimize such behavior. Additionally, the presence of film improves the mechanical strength and pliability of the fabric or non-woven substrate based materials, enhancing their suitability for use in laparoscopic procedures. In laparoscopic procedures, the composite is expected to be pushed through the trocar and sprung open into the body cavity more easily than either the substrate or film components individually.

The composite structures of the present invention often exhibit greater propensity and/or ability to stay in place during surgical procedures relative to existing hemostatic devices. For example, some fabric based products when used in multiple layers, or those in non-woven form may disintegrate or their parts may migrate during the application process. A substrate/film composite architecture of the present invention helps to maintain the physical integrity of the hemostatic materials, so it cannot fall prematurely to pieces, curve, or migrate during the procedure. Another advantage of the composite structures is that the device can be sutured in place.

The composite structure devices made from the method of the present invention also provide for the potential to use the film component for additional surgical functionality, such as to provide tissue support, to help in wound healing and/or to act as delivery carrier for bioactive agents.

Polymers useful in preparing the fabric or non-woven substrates in the laminated composite structures of the present invention include, without limitation, collagen, calcium alginate, chitin, polyester, polypropylene, polysaccharides, polyacrylic acids, polymethacrylic acids, polyamines, polyimines, polyamides, polyesters, polyethers, polynucleotides, polynucleic acids, polypeptides, proteins, poly (alkylene oxide), polyalkylenes, polythioesters, polythioethers, polyvinyls, polymers comprising lipids, and mixtures thereof. Preferred fibers comprise oxidized regenerated polysaccharides, in particular oxidized regenerated cellulose.

Preferably, oxidized polysaccharides are used to prepare wound dressings of the present invention. More preferably, oxidized cellulose is used to prepare fabrics used in wound dressings of the present invention. The cellulose either may be carboxylic-oxidized cellulose, or may be aldehyde-oxidized cellulose, each as defined and described herein. Even more preferably, oxidized regenerated cellulose is used to prepare fabric substrates used in wound dressings of the present invention. Regenerated cellulose is preferred due to its higher degree of uniformity versus cellulose that has not been regenerated. Regenerated cellulose and a detailed description of how to make regenerated oxidized cellulose is set forth in U.S. Pat. No. 3,364,200 and U.S. Pat. No. 5,180,398, the contents each of which is hereby incorporated by reference as if set forth in its entirety. As such, teachings concerning regenerated oxidized cellulose and methods of making same are well within the knowledge of one skilled in the art of hemostatic wound dressings.

Substrates, or fabrics utilized in conventional hemostatic wound dressings, such as Surgicel® absorbable hemostat; Surgicel Nu-Knit® absorbable hemostat; Surgicel SNoW® Absorbable Hemostat; and Surgicel® Fibrillar absorbable hemostat; all available from Johnson & Johnson Wound Management Worldwide, a division of Ethicon, Inc., Somerville, N.J., a Johnson & Johnson Company, as well as Oxycel® absorbable cellulose surgical dressing from Becton Dickinson and Company, Morris Plains, N.J., all may be used in preparing wound dressings according to the present invention. In certain embodiments, wound dressings of the present invention are effective in providing and maintaining hemostasis in cases of severe bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as hemophilia. Such wound dressings allow a patient to ambulate quicker than the current standard of care following, e.g. a diagnostic or interventional endovascular procedure.

The novel lamination processes of the present invention will use conventional pressure lamination process equipment and conventional film extrusion process equipment. The film extrusion process equipment will be operated at a sufficient temperature, pressure and extrusion speed to effectively provide for a desired film and output rate for a given polymer. For example, the temperature of the extrusion process equipment may be maintained at a temperature typically 100° C. to about 300° C., more typically 120° C. to about 250° C., and preferably about 160° C. to about 220° C. The film output rate for the process of the present invention will typically range from about 1 fpm to about 2,000 fpm, more typically about 5 fpm to about 100 fpm, and preferably about 6 fpm to about 20 fpm. The thickness of the film extruded in the process of the present invention will be sufficient to provide effective properties to the laminate structure. Such properties include tensile strength, tear-resistance and stiffness. Typically the film thickness will range from about 0.1 mils to about 10 mils, more typically about 0.2 mils to about 5.0 mils, and preferably about 1.0 mils to about 3.0 mils. The extruder pressure will typically be about 100 psi to about 5,000 psi, more typically about 500 psi to about 3,000 psi, and preferably about 1,000 psi to about 2,000 psi.

After extrusion from the process equipment the extruded film is preferably rolled up on a take-up roll with adjacent layers separated by a silicone release paper. The extruded film is then cut to lengths on a conventional cutting apparatus. The cut film is then either brought to a lamination station or stored under nitrogen. The film is laminated to a suitable substrate using a conventional lamination instrument using sufficient heat and pressure to provide for effective lamination of the film to the substrate. The time between the film extrusion and the lamination step will typically be about 5 seconds to about 10 minutes, more typically about 1 minute to about 8 minutes, and preferably about 2 minutes to about 5 minutes. The lamination temperature will typically be about 60° C. to about 140° C., more typically about 80° C. to about 130° C., and preferably about 100° C. to about 120° C. The lamination (Godet's speed) will typically be about 0.1 fpm to about 10 fpm, more typically about 0.2 fpm to about 5.0 fpm, and preferably about 0.5 fpm to about 2.0 fpm.

If desired, the extruded film may be moved to a lamination instrument without the intermediate step of rolling and cutting the film. In this variant of the process, the time between extrusion of the film and the lamination step will typically range from about 1 second to about 10 seconds, more typically about 2 seconds to about 6 seconds, and preferably about 3 seconds to about 5 seconds. After lamination in this continuous process, the laminate may be rolled or cut into discrete sections The extruded polymeric films at the time of lamination need to have crystallinity level of about 0% to about 10%, more preferably between 0% and 6%, and most preferably between 0% and 4%.

The novel laminating methods of the present invention and the laminated medical device constructs made from such processes have many advantages. The advantages include that no adhesive layer/film is needed for bonding, that a low processing temperature (120° C. or below) can be used to bond an absorbable or non-absorbable polymer film to a thermally sensitive substrate, which will prevent distortion and shrinkage of the substrate and minimize chemical degradation. The lack of an additional bonding layer will reduce the risk of adverse tissue reactions (less degradation products released such as free acids), improve biocompatibility, and decrease device stiffness—improve pliability. The use of method of the present invention will also significantly decrease production costs and greatly simplify the manufacturing steps of such a medical device.

The following examples are illustrative of the principles and practice of the present invention, although not limited thereto:

Example 1

Synthesis of the Segmented 75/25 Gly/Cap Copolymer

The segmented copolymer used in this example was made by the method previously described in the paper entitled, "Monocryl® Suture, a New Ultra-Pliable Absorbable Monofilament Suture" Biomaterials, Volume 16, Issue 15, October 1995, Pages 1141-1148. Its synthesis was also described in the patent literature such as U.S. Pat. No. 5,133,739 A and U.S. Pat. No. 8,278,409 B2. The disclosures of these references is incorporated herein by reference The final dried resin was a segmented A-B-A type copolymer having 75 mole % polymerized glycolide and 25 mole % polymerized ε-caprolactone units as determined by the nuclear magnetic resonance, NMR method. The dried resin exhibited an inherent viscosity, IV of 1.71 dL/g, as measured in hexafluoroisopropanol at 25° C. and at a concentration of 0.10 g/dL. Gel permeation chromatography, GPC analysis showed a weight average molecular weight of approximately 85,000 Daltons. The glass transition temperature, $T_g$, of the dried resin was 4.4° C., the melting point was 194° C., and the heat of fusion, $\Delta H_m$, was 45.3 J/g as determined by Differential Scanning calorimetry, DSC using first heat data and a heating rate of 10° C./min. Wide Angle X-ray Diffraction, WAXD analysis revealed that the dried resin was 45 percent crystalline.

Example 2

Selected Calorimetric Properties of the Dried Resin of Example 1

DSC measurements were conducted using a model Q20-3290 calorimeter from TA Instruments (New Castle, Del.) equipped with automatic sampler. In individual experiments, the dried, heat treated copolymer resin as described in Example 1 was placed into DSC pans, quenched below minus (−) 60° C., and heated at the constant heating rate of 10° C./min to determine its calorimetric properties (first heat properties); these included the glass transition temperature, $T_g$, the melting point, $T_m$ and the heat of fusion, $\Delta H_n$. From the second heat measurements (resin was melted at 240° C. and then quenched below −60° C.), values for $T_g$, $T_m$, $T_c$ (crystallization temperature), and $\Delta H_m$ were obtained that are independent from the previous heat treatment history. Data obtained using calorimetry measurements are displayed in Table 1.

TABLE 1

DSC Results during the First and Second Heat Runs on the Copolymer of Example 1 used to Describe the Present Invention

| | First Heat, DSC | | | Second Heat, DSC | | | | |
| --- | --- | --- | --- | --- | --- | --- | --- | --- |
| Example | $T_g$ (° C.) | $T_m$ (° C.) | $\Delta H_m$ (J/g) | $T_g$ (° C.) | $T_c$ (° C.) | $\Delta H_C$ (J/g) | $T_m$ (° C.) | $\Delta H_m$ (J/g) |
| 1 | 4.4 | 194 | 45.3 | 8.4 | 63.5 | 33.3 | 189 | 34.3 |

Crystallization characteristics were also assessed by the isothermal crystallization method. Isothermal crystallization kinetics analysis of the copolymer of Example 1 was conducted using the DSC technique. The dried, heat-treated copolymer resin, as described in Example 1, was placed into a DSC pan and completely melted at 240° C. for 2 minutes to remove any nucleation sites present in the sample. Subsequently, tested materials were rapidly cooled/quenched (cooling rate of −60° C./min) to the desired crystallization temperatures. The isothermal method assumes that no crystallization occurs before the sample reaches the test temperature; the data obtained supported this assumption. Crystallization behavior of the resin was characterized over a wide range of temperatures, between 50° C. and 110° C. Isothermal crystallization kinetics (at constant temperature) were monitored as a change in heat flow as a function of time. The isothermal heat flow curve was integrated to determine the crystallinity parameters. It is worth noting that the isothermal DSC runs were made in randomized order to avoid any bias.

The development of crystallinity with time can be accessed from the degree of crystallization, $\alpha$, which is expressed by the ratio $$\alpha = \frac{\Delta Ht}{\Delta H\infty} = \frac{\int_0^t \frac{dQ}{dt} dt}{\int_0^\infty \frac{dQ}{dt} dt} \quad (1)$$

where $dQ/dt$ is the respective heat flow; $dH_t$, the partial area between the DSC curve and the time axis at time t; and $dH_\infty$, the total area under the peak and corresponds to the overall heat of crystallization. The degree of crystallization $\alpha$, is then the crystalline volume fraction developed at time t.

After performing the integration of the heat flow/time curve, the crystallization half-time, $t_{1/2}$, can be determined. The crystallization half-time is the time needed to reach 50 percent crystallinity of the total amount developed during the isothermal run. In order to express crystallization kinetics, a reciprocal crystallization half-time was presented as a function of crystallization temperature. The data from isothermal measurements are shown in Table 2 below. The fastest kinetics for the examined resins was observed at approximately 100° C.

TABLE 2

DSC Results during the Isothermal crystallization Runs on the Copolymer of Example 1 used to Describe the Present Invention

| Temperature (° C.) | $t_{1/2}$ (min) | $1000/t_{1/2}$ (min⁻¹) | Slope [W/(g × min)] | $\Delta H_C$ (J/g) |
| --- | --- | --- | --- | --- |
| 50 | No detected crystallization by DSC | | | |
| 55 | Crystallization detected but difficult to quantify | | | |
| 60 | 22.0 | 45.5 | 0.00065 | 25.1 |
| 65 | 16.2 | 61.7 | 0.00129 | 18.8 |
| 70 | 13.0 | 76.9 | 0.00260 | 29.2 |
| 75 | 12.5 | 80.0 | 0.00318 | 32.2 |
| 80 | 10.8 | 92.6 | 0.00530 | 33.3 |
| 85 | 9.4 | 106.5 | 0.00744 | 34.2 |
| 90 | 8.5 | 117.6 | 0.01013 | 35.1 |
| 95 | 8.2 | 122.0 | 0.01116 | 35.5 |
| 100 | 7.1 | 140.8 | 0.01266 | 34.4 |
| 105 | 7.9 | 126.6 | 0.01234 | 36.0 |
| 110 | 9.0 | 111.1 | 0.01031 | 36.5 |

Example 3

Film Formation by the Melt Extrusion of the Resin of Example 1

The melt film extrusion of the resin of Example 1 was carried out using a melt extruder Model KN125 manufactured by Davis Standard Corp., Pawcatuck, Conn. 06379, U.S.A, outfitted with a film die. A die gap of 6 mils was used in all film extrusion runs. Extruder temperatures throughout the different barrel zones ranged from 180 to 210° C., with the die temperature kept at 220° C. The screw speed was set to 15.8 rpm for 1-mil thick film with the linear speed of the pull out roll maintained at 10.4 fpm. Similarly, for the 2-mil thick film the screw speed was 19.1 rpm, while the linear speed of the pull out roll was maintained at 6.0 fpm. During film collection, a silicone release paper dispensed from a roll stand was used to separate the film layers being wound on the take-up roll. After extrusion, the film with corresponding silicone release paper was cut to convenient lengths and either brought to the lamination instrument immediately after extrusion, or stored under nitrogen for a longer period of time. The thicknesses of the films produced were determined to be 1.0 and 2.0 mil.

Example 4

Examination of the Crystallization Properties of the Films Made in Example 3

The calorimetric properties of the unannealed and annealed films of the Example 3 were determined using the first and the second heat DSC methods. Summary of the results is shown in Table 3 below.

TABLE 3

Thermal (Calorimetric) Properties of Unannealed and Annealed 2-mil Extruded Film from Example 3

| | | First Heat | | | | |
|---|---|---|---|---|---|---|
| Film ID | Description | $T_g$ (° C.) | $T_C$ (° C.)/ $\Delta H_C$ (J/g) | $T_m$ (° C.) | $\Delta H_m$ (J/g)/ | % Cryst.** |
| EX. 3 - Unannealed | Unannealed film from Example 3 stored at 25° C. for 48 hours | 6.5 | none | 191.3 | 45.9 | 46 |
| EX. 3 - Annealed | Annealed film from Example 3 @ 105° C./8 hrs | 3.0 | none | 191.5 | 46.8 | 47 |

| | | Second Heat* | | | |
|---|---|---|---|---|---|
| Film ID | Description | $T_g$ (° C.) | $T_C$ (° C.)/ $\Delta H_C$ (J/g) | $T_m$ (° C.) | $\Delta H_m$ (J/g) |
| EX. 3 - Unannealed | Unannealed film from Example 3 stored at 25° C. for 48 hours | 7.5 | 63.9/32.4 | 191.0 | 39.9 |
| EX. 3 - Annealed | Annealed film from Example 3 @ 105° C./8 hrs | 7.7 | 63.5/35.8 | 191.4 | 39.9 |

*The second heat DSC measurements were started by melting the resin at 240° C. for 2 minutes, with a subsequent quench (−60° C./min) to −60° C., followed by the constant heating scan at 10° C./min
**The percent crystallinity was calculated from the heat of fusion of 100% crystalline PGA material ($\Delta H_m$ = 12 KJ/mole, which is equivalent to 103 J/g); [refs.: *Biomedical Engineering Fundamentals* by Joseph D. Bronzino, Donald R. Peterson; *Wound Closure Biomaterials and Devices* edited by Chih-Chang Chu, J. Anthony von; *Biomaterials: Principles and Practices* edited by Joyce Y. Wong, Joseph D. Bronzino, Donald R.; *Biotextiles as Medical Implants* edited by M W King, B S Gupta, R Guidoin; *The Biomedical Engineering Handbook 1* by Joseph D. Bronzino; *Surfaces and Interfaces for Biomaterials* edited by P Vadgama]

As indicated in Table 3, both unannealed and annealed films made in Example 4 contain relatively high level of crystallinity (46% and 47%, respectively), as well as high melting points (both around 191° C.) as determined from the first heat measurement. From the second heat scan both films showed lower level of crystallinity (around 40%). This is due to the fact that during the experiment, the thermal history was first erased (sample was brought into amorphous phase), followed by the step in which the crystallinity was developed only during the heating scan from the quench with relatively fast heating rate of 10° C./min.

In order to understand further the crystallization kinetics of these films, we conducted the following set of experiments. The piece of the film made in Example 3 was placed in a DSC pan, heated to 240° C. for two minutes to erase any thermal history, and then brought quickly to room temperature, where it spent a specified amount of time developing crystal morphology. After this "dwelling" period, the sample was heated at 10° C./min to above its melting point, 240° C. During this heating step (first heat measurement), additional crystallization will occur followed by the subsequent melting transition. The difference between the peak areas under the heat of fusion (melting transition) and the heat of crystallization is directly proportional to the amount of crystallinity that a sample developed by being exposed to room temperature. The summary of data from this set of experiments is given in Table 4 below. The last column in Table 4 shows the amount of crystallinity developed during the residence time at room temperature for a given sample.

TABLE 4

Isothermal Crystallization Study of 75/25 Gly/Cap Copolymer resin of Example 1 by DSC Method as a Function of Residence Time at Room Temperature

| | Time spent at 22° C. | First heat* | | | | | |
|---|---|---|---|---|---|---|---|
| Polymer ID | (min) | $T_c$ (° C.) | $\Delta H_c$ (J/g) | $T_m$ (° C.) | $\Delta H_m$ (J/g) | $\Delta H_m - \Delta H_c$ (J/g) | % Cryst.** |
| EX 3 - 5 min | 5 | 93.6 | 32.2 | 191.1 | 36.6 | 4.4 | 4.5 |
| EX 3 - 10 min | 10 | 92.3 | 30.6 | 192.6 | 37.0 | 6.4 | 6.6 |
| EX 3 - 30 min | 30 | 89.9 | 29.8 | 191.5 | 39.6 | 9.8 | 10.1 |
| EX 3 - 120 min | 120 | 88.5 | 28.5 | 191.4 | 39.3 | 10.8 | 11.1 |
| EX 3 - 16 hrs | 960 | 62.5 | 24.0 | 191.2 | 39.9 | 15.9 | 16.4 |

*The first heat DSC measurements were started by melting the resin at 240° C. for 2 minutes, with a subsequent quench (−60° C./min) to 22° C., and isothermal dwelling at that temperature for a given amount of time, followed by the constant heating scan at 10° C./min
**The percent crystallinity was calculated from the heat of fusion of 100% crystalline PGA material ($\Delta H_m$ = 12 KJ/mole, which is equivalent to 103 J/g); [refs.: *Biomedical Engineering Fundamentals* by Joseph D. Bronzino, Donald R. Peterson; *Wound Closure Biomaterials and Devices* edited by Chih-Chang Chu, J. Anthony von; *Biomaterials: Principles and Practices* edited by Joyce Y. Wong, Joseph D. Bronzino, Donald R.; *Biotextiles as Medical Implants* edited by M W King, B S Gupta, R Guidoin; *The Biomedical Engineering Handbook 1* by Joseph D. Bronzino; *Surfaces and Interfaces for Biomaterials* edited by P Vadgama]

As shown in Table 4, the amount of crystallinity that films were able to develop at room temperature was relatively small (less than 7%) during the 10 minutes or shorter residence time. However, with longer dwelling, the amount of crystallinity progressively increased. In addition, samples that had longer residence time at room temperature exhibited faster or easier crystallization during the first heating scan. This is indicated in the third column in Table 4, as the crystallization peak shifted accordingly to lower temperatures.

Example 5

Lamination of Composite Structures Having Different Substrates and a Semi-Crystalline Film Made from 75/25 Gly/Cap Mole % (Non-Inventive Example)

Films made from the copolymer resin of Example 1 having thickness of 1 and 2 mil (described in Example 3) were laminated onto a variety of ORC based substrates, available from Ethicon Inc., under the trade name of Surgicel Classic®, Surgicel NuKnit®, Surgicel Snow®, as well as a polypropylene (PP)-based mesh for hernia repair applications. The films were aged or matured at room temperature; the elapsed time from the actual film extrusion process to the time of lamination was set to be at least 48 hours or longer. The lamination was done using the heating set of Godets with the nipping roll combination. Laminations were performed at various Godet's temperatures ranging from 120 to 200° C. The roll speed was generally kept between 0.5 and 1 FPM for both 1-mil and 2-mil films. It is important to mention that the low temperature lamination is highly desired to keep oxidized regenerated cellulose (ORC) materials free of degradation, as well as for polypropylene (PP) meshes to avoid any heat related distortions. For ORC line of products the temperature of 120° C. or below is considered safe for lamination, while 145-150° C. is considered upper temperature limit for polypropylene-based meshes.

All attempts to laminate aged 75/25 Gly/Cap films (1 and 2-mil) onto any substrate at temperatures lower than 150° C. failed due to immediate delamination (lack of bonding). This is due to the fact that the melting point of the film was 191° C. There were some partial melting and bonding of the film on substrates at temperatures higher than 150° C., but soon delamination occurred during handling. Most importantly, ORC-based substrates turned yellowish, indicating the onset of degradation processes, while PP mesh heavily distorted due to extensive shrinkage.

Example 6

Lamination of Composite Structures Having Different Substrates and Freshly Extruded Low Crystallinity Films Made from 75/25 Gly/Cap Mole % at Low Processing Temperatures (Inventive Example)

As used herein, the term "freshly extruded" is defined to mean an absorbable, semi-crystalline polymeric film that has been laminated on a substrate within 10 minutes or less following its extrusion step. In order to examine the lamination of a 75/25 Gly/Cap film immediately after extrusion step described earlier in Example 3, the piece of the rectangular polymer film exiting the last set of extrusion Godet's was cut and brought to the lamination instrument described in Example 4. A series of lamination procedures were conducted next on each substrate using low Godet's temperature of 120° C. at the following time intervals: 2, 5, 10, and 30 minutes from the end of film extrusion.

Unexpectedly, all film/substrate combinations that were marked with the time intervals 2, 5 and 10 minutes exhibited perfect laminations (bonding) at a low processing temperature of 120° C. However, certain test combinations did not produce optimal results (partial delamination was observed) that were processed 30 min after film extrusion. The samples that were observed to produced good lamination (2, 5, and 10 minutes) were subsequently placed in the stability chamber supplied with the nitrogen flow at room temperature for 72 hours to develop additional crystal morphology. Following 72-hour room temperature aging the film/ORC film/PP-mesh composites were examined for handling characteristics.

Produced laminated composites made using the process of the present invention exhibited excellent handling properties, and no delamination of 75/25 Gly/Cap films were observed in any of the prepared combinations marked 2, 5, and 10 minutes. In addition, no distortion or wrinkling of the ORC or PP fabric was observed. Using extensive physical treatments, including repeated bending procedures, pulling and other subjective handling operations, the film/ORC and film/PP structures did not tear or showed any sign of damage. Finally, due to low lamination temperature of 120° C., no discoloration was observed in any of the ORC fabric.

Although this invention has been shown and described with respect to detailed embodiments thereof, it will be understood by those skilled in the art that various changes in form and detail thereof may be made without departing from the spirit and scope of the claimed invention.

We claim:

1. A method of making a laminated medical device construct, comprising:
    a) extruding a polymer film having a semi-crystalline structure and a melting point temperature of 140° or higher, a glass transition temperature below 25° C., and a crystallinity, said polymer film being crystallizable at room/ambient conditions;
    b) laminating the polymer film directly to a substrate, said substrate being thermally sensitive and polymeric, to form the laminated medical device construct by conducting a thermal/pressure laminating step within about 10 minutes after the polymer film has been extruded wherein the polymer film has a crystallinity of about 10% or less in order to laminate said polymer film onto a substrate at a temperature of about 120° C. or lower, wherein the substrate is not damaged and the polymer film is effectively laminated to the substrate.

2. The method of claim 1, wherein the substrate is selected from the group consisting of non-woven substrate, woven substrate and mesh substrate.

3. The method of claim 1 wherein the polymer film comprises a polymer material selected from the group consisting of copolymers of lactide or glycolide as major components with one or more other components including caprolactone, poly (p-dioxanone); trimethylene carbonate (TMC), polyethylene glycol, and polyether ester formulations.

4. The method of claim 1, wherein the polymer film comprises a polymer material selected from the group consisting of polypropylene, polyethylene, polyethylene terephthalate, and Nylon.

5. The method of claim 1, wherein the polymer film comprises a copolymer of glycolide and epsilon-caprolactone in the molar ratio of about 75 to about 25%, respectively.

6. The method of claim 1, wherein the substrate comprises a material selected from the group consisting of collagen, calcium alginate, chitin, polyester, polypropylene, polysaccharides, polyacrylic acids, polymethacrylic acids, polyamines, polyimines, polyamides, polyesters, polyethers, polynucleotides, polynucleic acids, polypeptides, proteins, poly (alkylene oxide), polyalkylenes, polythioesters, polythioethers, polyvinyls, polymers comprising lipids, oxidized regenerated cellulose, and mixtures thereof.

7. The method of claim 1, wherein the lamination is performed off-line.

8. The method of claim 1, wherein the lamination is performed in-line reel-to-reel.

9. The method of claim 5, wherein the polymer film has a crystallinity that changes from about 0 to about 10% in the first 30 minutes after extrusion, and above 20% for a dwell/aging time longer than 24 hours.

10. The method of claim 1, wherein the extruded film is rolled and cut into pieces prior to lamination to the substrate.

\* \* \* \* \*